(12) United States Patent
Tatterfield et al.

(10) Patent No.: US 10,195,321 B2
(45) Date of Patent: Feb. 5, 2019

(54) LINER AND BREAST INTERFACE FOR A BREAST PUMP

(71) Applicant: KONINKLIJKE PHILIPS N.V., Eindhoven (NL)

(72) Inventors: Andrew John Roy Tatterfield, Eindhoven (NL); Christopher John Padbury, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 29 days.

(21) Appl. No.: 14/771,585

(22) PCT Filed: Mar. 5, 2014

(86) PCT No.: PCT/EP2014/054197
§ 371 (c)(1),
(2) Date: Aug. 31, 2015

(87) PCT Pub. No.: WO2014/035553
PCT Pub. Date: Sep. 12, 2014

(65) Prior Publication Data
US 2016/0008526 A1    Jan. 14, 2016

Related U.S. Application Data

(60) Provisional application No. 61/772,597, filed on Mar. 5, 2013.

(30) Foreign Application Priority Data

Mar. 5, 2013  (EP) .................................... 13157739

(51) Int. Cl.
*A61M 1/06*       (2006.01)

(52) U.S. Cl.
CPC .................................. *A61M 1/066* (2014.02)

(58) Field of Classification Search
CPC ........ A61M 1/06; A61M 1/066; A61M 1/068; A61J 13/00
See application file for complete search history.

(56) References Cited

U.S. PATENT DOCUMENTS

| 4,772,262 A | 9/1988 | Grant |
| 4,799,922 A * | 1/1989 | Beer ....................... A61M 1/06 |
| | | 119/14.49 |

(Continued)

FOREIGN PATENT DOCUMENTS

| EP | 0466462 A1 | 1/1992 |
| WO | 2010146501 A1 | 12/2010 |

*Primary Examiner* — Emily Schmidt
*Assistant Examiner* — Alexandra Lalonde

(57) ABSTRACT

A liner (100) for use in a breast interface (70) comprises a front section (110) including a front wall part (112) defining a breast contact surface (118) and an opening (116b) provided in the breast contact surface. The breast contact surface (118) is configured to abut a woman's breast during use, while a nipple of the breast protrudes at least partially through the opening (116b). The breast interface further comprises a rear section (170), connected to the front section (140), that includes a tubular wall part (171) having a rear end opening. The front and rear sections (110, 170) together define a milk passage (190) that extends from the opening (116b) in the breast contact surface (118) to the rear end opening of the tubular wall part (171), wherein the milk passage slopes downwardly in the rearward direction.

20 Claims, 8 Drawing Sheets

(56) References Cited

U.S. PATENT DOCUMENTS

| | | | | |
|---|---|---|---|---|
| 6,673,037 B1* | 1/2004 | Silver | ................... | A61M 1/06 604/74 |
| 6,974,439 B1* | 12/2005 | McKendry | .............. | A61M 1/06 119/14.02 |
| 7,101,350 B2 | 9/2006 | Ytteborg | | |
| 7,354,418 B2 | 4/2008 | Lee | | |
| 8,961,454 B2* | 2/2015 | Chen | ....................... | A61M 1/06 604/73 |
| 2005/0080376 A1* | 4/2005 | Myers | ................... | A61M 1/06 604/74 |
| 2005/0222536 A1* | 10/2005 | Silver | .................. | A61M 1/064 604/74 |
| 2006/0116632 A1 | 6/2006 | Gillian | | |
| 2007/0088250 A1* | 4/2007 | Silver | .................. | A61M 1/064 604/74 |
| 2009/0171270 A1* | 7/2009 | Rohrig | ................... | A61M 1/06 604/74 |
| 2010/0121266 A1* | 5/2010 | Bryan | .................... | A61M 1/06 604/74 |
| 2012/0004604 A1* | 1/2012 | Van Der Kamp | .... | A61M 1/066 604/74 |

* cited by examiner

LINER AND BREAST INTERFACE FOR A BREAST PUMP

This application is the U.S. National Phase application under 35 U.S.C. § 371 of International Application No. PCT/EP2014/054197, filed on Mar. 5, 2014, which claims the benefit of European Application No. 13157739.7 filed on Mar. 5, 2013 and U.S. Provisional Application 61/772,597 filed Mar. 5, 2013. These applications are hereby incorporated by reference herein.

TECHNICAL FIELD OF THE INVENTION

The present disclosure relates to a breast interface for use in a breast pump, said breast interface including a flexible liner and a generally rigid liner support frame.

BACKGROUND OF THE INVENTION

Breast pumps are well known in the art. A breast pump may typically comprise a breast interface or breast shield that fits over a breast, and a vacuum pump that is connectable to the breast interface for generating a vacuum (negative pressure) within the breast interface. The vacuum may cause the breast interface to pull on the breast and to massage it, so as to extract milk. The extracted milk may drain from the breast interface into a milk receptacle, which may be detachably connected to the breast pump.

US 2009/0171270 discloses an attachment for a milk pump. The attachment has a funnel-shaped application portion with a longitudinal axis and a connecting portion adjoining the application portion and adjoined by a fixing portion. The application portion may be arranged to be pivotable relative to the fixing portion in a manner that the longitudinal axis of the application portion can be arranged in an angular position deviating from 180° relative to the rotational axis of the fixing portion.

In US 2006/0116632 a reclining breast pumping system is disclosed that includes a breast shield that forms a passageway. Material adjacent to one end of the passageway forms a flange that is shaped to fit onto a woman's breast around the nipple. The material extending from the other end of the passageway forms a tube. A plane parallel to the areola of the breast is substantially angled from a plane perpendicular to the axis of the tube, defining a tube deviation angle.

US 2005/0222536 discloses a breast shield for a breast pump. The first end of the breast shield may have a wide cross-section and may be generally circular in cross sectional shape. The first end further includes a circumferential flange. A nipple tunnel opens into the first end and extends longitudinally towards the second and downstream end. The overall body of the breast shield may be generally cylindrical and the breast shield may be curved along its longitudinal length.

U.S. Pat. No. 6,974,439 discloses a device for expressing milk, comprising at least one expresser with a cup assembly which fits on a breast. The cup assembly includes a bell housing, a relatively soft donut shaped pad and a flexible liner. The liner may have a relatively narrow section near the milk inlet opening and a wider section between the narrow section and the outlet end of the cup assembly.

SUMMARY OF THE INVENTION

A problem associated with conventional breast interfaces is that they may require a woman using it to lean forward, so as to ensure that milk expressed from her breast flows towards and into the milk receptacle. The forward leaning posture may become uncomfortable as a single milk-expressing session may last a while, sometimes in excess of half an hour.

It is an object of the present disclosure to provide for a liner, and for a breast interface comprising such a liner, that overcomes or at least mitigates the aforementioned problem.

To this end, a first aspect of the present disclosure is directed to a liner for use in a breast interface. The liner may comprise a front section including a front wall part defining a breast contact surface and an opening provided in said breast contact surface. The breast contact surface may be configured to abut a woman's breast during use, while a nipple of the breast protrudes at least partially through said opening. The liner may also comprise a rear section that is connected to the front section, and that includes a tubular wall part having a rear end opening for discharging milk from the liner. The front and rear sections may together at least partly define a milk passage that extends from the opening in the breast contact surface to the rear end opening of the tubular wall part. Also, the liner may be associated with a use orientation in which a longitudinal axis of the front section—which may typically extend substantially perpendicular to a plane of the opening in the breast contact surface—extends substantially horizontally, while the tubular wall part of the rear section has a lower inner surface portion that partially bounds the milk passage, and that—in said use orientation, seen in a rearward direction—slopes downwardly relative to the longitudinal axis. The tubular wall part of the rear section may have a tear drop-shaped cross-section. A narrower part of the tear drop-shaped cross section may define a gully, whose bottom is defined by the lower inner surface portion.

In use, the presently disclosed liner may be held in its use orientation, such that the breast contact surface of the front section of the liner is in contact with a woman's breast. While the longitudinal axis of the front section of the liner may extend substantially horizontally, the lower inner surface portion of the tubular wall part of the rear section may slope downwardly relative thereto. Accordingly, milk expressed from the breast may be naturally guided through the milk passage, towards the rear end opening of the tubular wall part, to be discharged into a milk receptacle that may be operably connected thereto. The natural flow of milk through the liner due to the action of gravity overcomes the need for the woman expressing milk to lean forward.

In preferred embodiments of the liner, the lower inner surface portion may extend over substantially an entire length of the tubular wall part of the rear section. The lower inner surface portion may slope downwardly relative to the longitudinal axis of the front section at a preferably substantially constant slope angle ($\varphi$). In the use orientation—the lower inner surface portion may preferably have an average downward slope angle in the range of 10-45 degrees relative to the longitudinal axis of the front section.

A second aspect of the present disclosure is directed to a breast interface. The breast interface may comprise a liner support frame defining an interior liner support frame space configured to receive at least part of a liner. The liner support frame may include a front ring, a rear ring, and at least one arm interconnecting the front ring and the rear ring such that they are axially spaced apart. The breast interface may also comprise a liner according to the first aspect of the present disclosure, wherein the front section of the liner is configured to engage the front ring of the liner support frame, while the tubular wall part of the rear section of the liner may be configured to be fittingly received by the rear ring of the liner support frame.

In a particularly conveniently assemblable elaboration of the breast interface, a rear end of the tubular wall part of the rear section of the liner may be provided with a first annular flange that has an outer diameter that is greater than an inner diameter of the rear ring of the liner support frame, and that, in an assembled condition of the breast interface, abuts the rear ring on end. In addition, the rear ring may be a split rear ring including at least two complementary circumferential rear ring portions that are rearrangeable relative to each other to facilitate passage of a flanged rear end of a liner.

A third aspect of the present disclosure is directed to a breast pump including a breast interface according to the second aspect of the present disclosure.

These and other features and advantages of the invention will be more fully understood from the following detailed description of certain embodiments of the invention, taken together with the accompanying drawings, which are meant to illustrate and not to limit the invention.

DETAILED DESCRIPTION

Figure 1A:
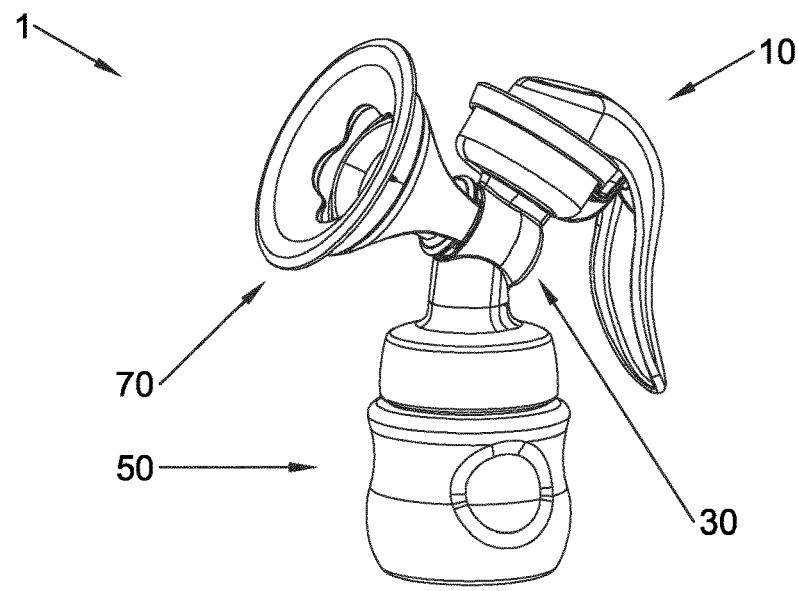
FIGS. 1A-B schematically illustrate an embodiment of a breast pump according to the present disclosure, including a first exemplary embodiment of a breast interface for contacting a woman's breast, once in a perspective view (FIG. 1A) and once in a cross-sectional, partly exploded side view (FIG. 1B)
Figure 1B:
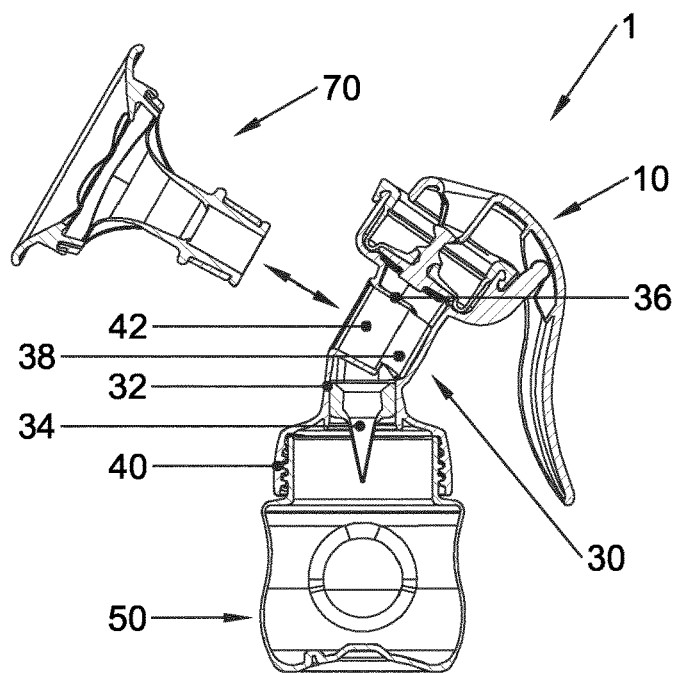
Figure 2A:
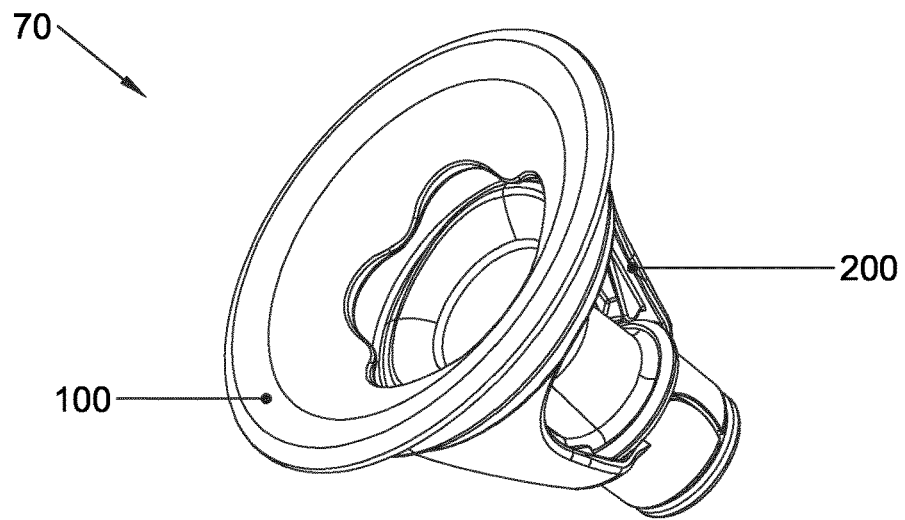
FIGS. 2A-D schematically illustrate the first exemplary embodiment of the breast interface of the breast pump shown in FIG. 1, including both a liner and a liner support frame, in a perspective view (FIG. 2A), a side view (FIG. 2B), and two mutually perpendicular cross-sectional side views (FIG. 2C-D), respectively.
Figure 2B:
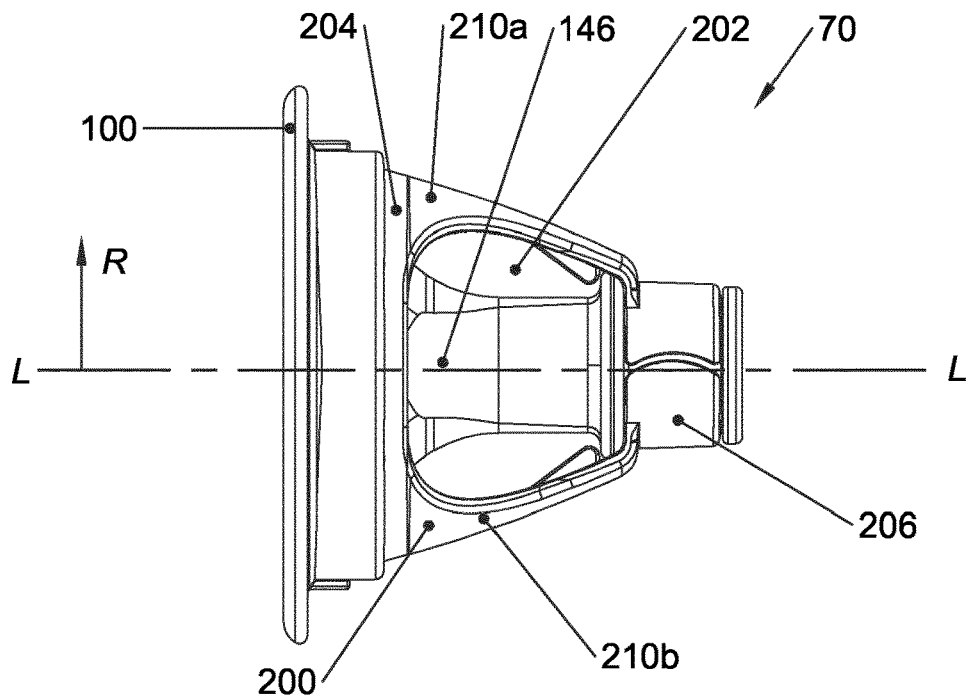
Figure 2C:
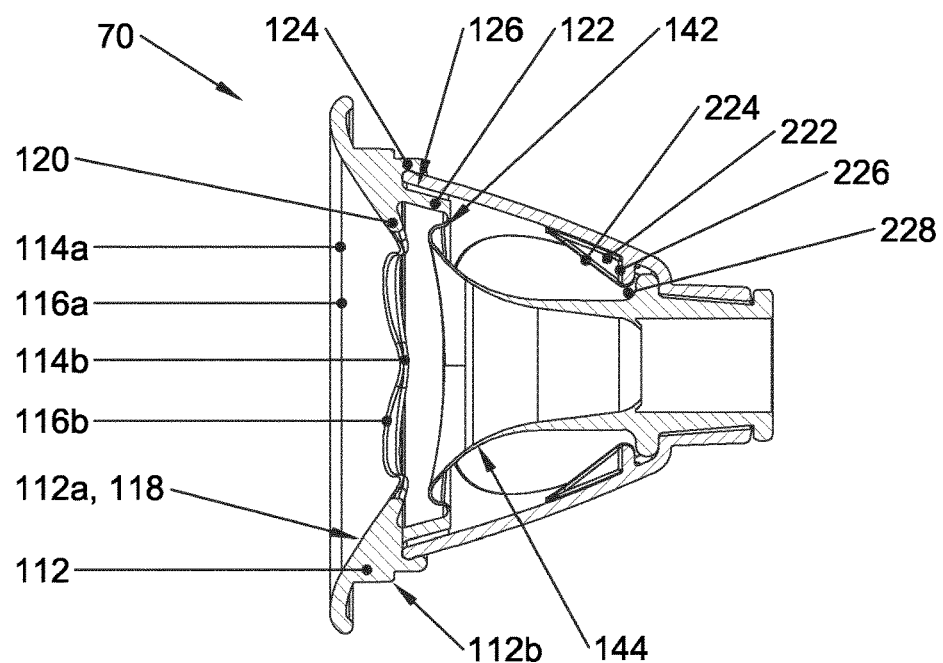
Figure 2D:
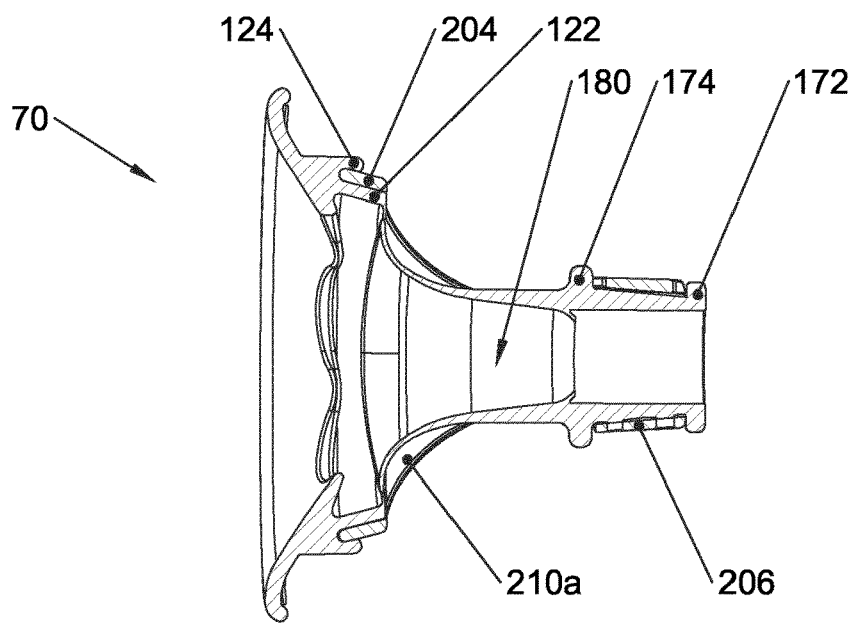
Figure 3A:
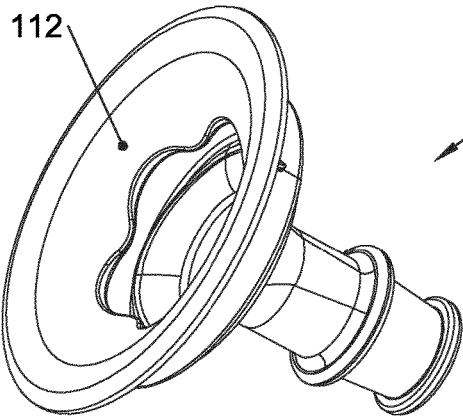
FIGS. 3A-D schematically illustrate, in isolation, the liner of the first exemplary embodiment of the breast interface shown in FIG. 2 in a perspective view (FIG. 3A), a side view (FIG. 3B), a front view (FIG. 3C) and a rear view (FIG. 3D), respectively.
Figure 3B:
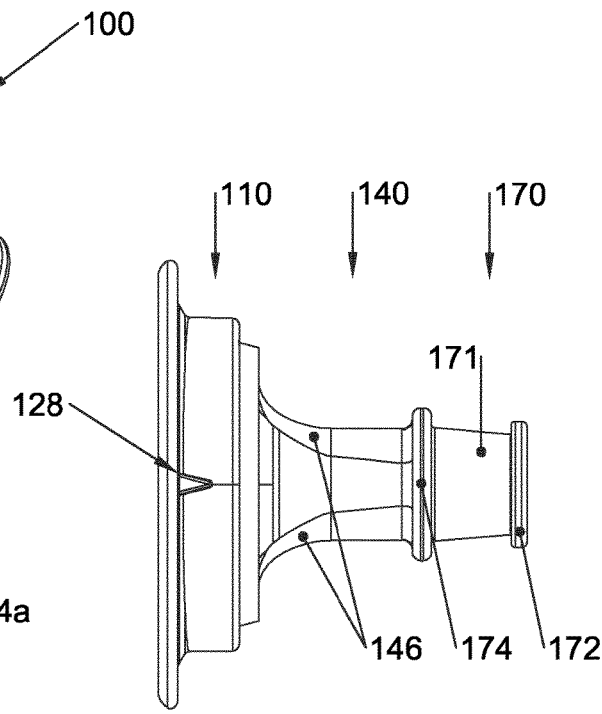
Figure 3C:
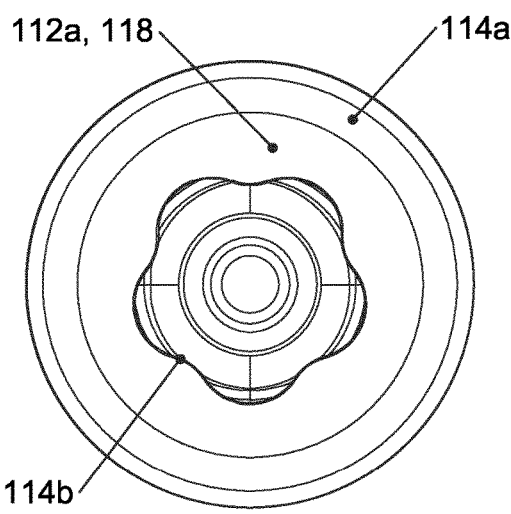
Figure 3D:
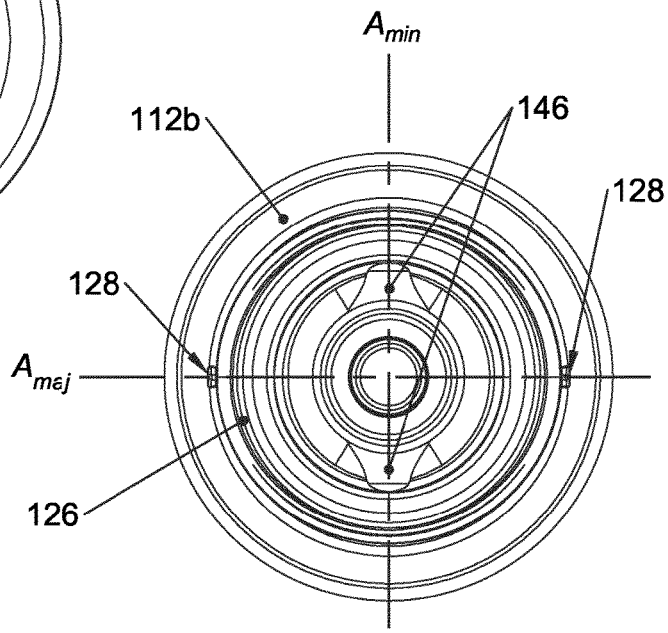

FIG. 1 schematically illustrates in a perspective view an exemplary breast pump 1 according to the present disclosure. The breast pump 1 may include a vacuum pump 10, a coupler 30, a milk receptacle 50, e.g. a milk bottle, and a first exemplary embodiment of a breast interface 70.

The coupler 30 may include a first, generally vertically extending tubular segment 32 defining a first channel 34, and a second tubular segment 36 extending transverse to and/or outward from the first tubular segment 32 and defining a second channel 38 that is in fluid communication with the first channel 34. At the lower end of the first tubular segment 32, the coupler 30 may include a threaded socket 40 with an inner thread for threaded connection to the milk receptacle 50, whose upper end may be provided with a complementary outer thread. The opposite upper end of the first tubular segment 32 may connect to a vacuum pump 10 configured to apply a vacuum to the first and second channels 34, 38. The vacuum pump 10 may be a manual vacuum pump, as in the depicted embodiment, or an electric vacuum pump, and in itself be of a conventional design that is not elaborated upon here. The outward end of the second tubular segment 36 may further define a reception passage 42 configured to press-fittingly receive a rear end of the breast interface 70, such that the vacuum pump 10, the milk receptacle 50 and the breast interface 70 are in pneumatic communication via the coupler 30, while fluid communication is possible between the latter two. It is understood that different embodiments of the breast pump 1 may include couplers 30 having different shapes and configurations than that described and illustrated, and that the types of connections used to connect in particular the vacuum pump 10 and the milk receptacle 50 to the coupler 30 may be of any suitable type, e.g. threads, snap-fits, etc.

Conceptually, the breast interface 70 may comprise two components: a flexible liner 100 and a sturdy, relatively stiff or rigid liner support frame 200. The liner 100 and the liner support frame 200 may typically be formed as two separate structural components that need to be assembled together upon use to form the breast interface 70, and that may be taken apart afterwards to facilitate cleaning and replacement of one of the components. It is contemplated, however, that the liner 100 and liner support frame 200 may alternatively be integrally formed as a single structural component, e.g. co-moulded, so as to reduce the number of structural parts of the breast interface 70.

Below, the construction of the liner 100 and the liner support frame 200 of the breast interface 70 according to the present disclosure are discussed. First, the liner 100 and the liner support frame 200 of the first exemplary embodiment of the breast interface 70 shown in FIGS. 1-4 will be described, taking account of some contemplated variations. Subsequently, particular advantageous second, third and fourth exemplary embodiments of the breast interface 70 will be described with reference to FIGS. 5, 6 and 7, respectively.

Referring now to in particular FIGS. 2-3, the liner 100 may comprise three, typically integrally formed sections: a front section 110, a middle section 140, and a rear section 170. Each section may include at least one wall part that defines it.

The front section 110 of the liner 100 may include a rearward tapering, generally conical or cup-shaped front wall part 112 that extends between a forward, radially outer circumferential edge 114a bounding a forward opening 116a and a rearward, radially inner circumferential edge 114b bounding a central rearward opening 116b. Axially in between the circumferential edges 114a, 114b, a front side 112a of the front wall part 112 may define a generally conical breast contact surface 118.

The front section 110 of the liner 100 may further include an annular base wall part 122. The base wall part 122 may connect to a rear side 112b of the front wall part 112, at a radial position in between those of the forward and rearward circumferential edges 114a, 114b thereof, and extend from the rear side 112b of the front wall part 112 in a rearward direction. Accordingly, along their annular join, the front wall part 112 may be considered to extend radially inwardly beyond the base wall part 122, so as to form an annular (milk) backflow barrier 120.

The front section 110 may also include an annular lip wall part 124. Like the annular base wall part 122, the lip wall part 124 may connect to the rear side 112b of the front wall part 112b, at a radial position in between those of the forward and rearward circumferential edges 114a, 114b thereof, and extend from the rear side 112b of the front wall part 112 in a rearward direction. The annular lip wall part 124 and the annular base wall part 122 may run circumferentially parallel to each other, wherein the annular lip wall part 124 may extend at a greater radial coordinate, such that an annular groove 126 is defined in between the radially outer lip wall part 124 and the radially inner base wall part 122. The annular groove 126 may be configured to receivingly engage a front ring 204 of the liner support frame 200 (see FIGS. 2C-D), and thus have a (generally radial) width that is equal to or slightly smaller than a (generally radial) width of the front ring 204.

During use, the front section 110 of the liner 100 may be placed over a woman's breast, such that an interior space bounded by the conical front wall part 112 serves as a receptacle for the breast, and the breast is at least partly received within this interior space. The areola and the nipple of the breast, or at least the latter, may then protrude through the central rearward opening 116b in the front wall part 112, while the breast contact surface 118 may act as a stop that abuts a circum-areolar portion of the breast to prevent the breast from being inserted or sucked into the liner 100 any deeper.

The front section 110 of the liner 100 may be configured such that it substantially maintains its shape during use; i.e. it is intended not to deform significantly. However, the aforementioned middle section 140 of the liner 100, which may be connected to the rear end (of the base wall part 122 of) the front section 110, may be configured to collapse bilaterally onto the nipple of the breast during operation. To help ensure that the middle section 140 of the liner 100 collapses bilaterally in a controlled fashion, the annular groove 126 in the front section 110 of the liner 100 and the front ring 204 of the liner support frame 200 to be received therein may have different circumferential shapes. The difference in shapes may preferably be such that, when, during assembly of the breast interface 70, the front ring 204 is inserted into the annular groove 126, the front section 110 (and hence the middle section 140 connected thereto) is stretched/widened along a first radial direction, and compressed/narrowed along a second radial direction substantially perpendicular to said first radial direction.

In one embodiment, for instance, the annular groove 126 may have a circular circumferential shape, while the front ring 204 of the liner support frame 200 may have an elliptical shape. The elliptical shape of the front ring 204 may be described in terms of a major axis and a minor axis, both of which axes may be radially extending axes in the context of the breast interface 70 as they may extend perpendicularly to a longitudinal axis L thereof. The major axis may have a length that is slightly larger than the diameter of the circular groove, while the minor axis may have a length that is slightly smaller than the diameter of the circular groove. Consequently, the front section 110 of the liner 100 will be pre-stressed upon insertion of the front ring 204 into the annular groove 126. That is, it will be stretched along the major axis of the elliptical front ring 204, and compressed along the minor axis of the front ring 204. This pre-stressing of the front section 110, and hence of the middle section 140 connected thereto, promotes the bilateral collapse of the middle section along the minor axis.

A drawback of the aforementioned embodiment of the breast interface 70, including a circular groove 126 and an elliptical front ring 204, is that it may be susceptible to rotational misalignment of the minor and/or major axes of the front ring 204 with a certain wall stiffness distribution of the middle section 140 of the liner 100. As will be clarified below, the middle section 140 of the liner 100 may include elongate, relatively stiff wall part portions 146, e.g. ribs, that extend on opposite sides of the wall parts 142, 144 of the middle section 140 in order to promote a controlled bilateral collapse of the liner 100 when the interior 180 of the liner is evacuated. In an embodiment including such ribs 146, the ribs of the middle section 140 may preferably be rotationally aligned with the major axis of the front ring 204, such that the two features—i.e. the wall stiffness distribution, and the shape difference between the circular annular groove 126 and the elliptical front ring 204—cooperate and enhance each other in producing a bilateral collapse. During assembly of the breast interface 70, however, the major and minor axes of the front ring 204 of the liner support frame 200 may be easily misaligned with the wall stiffness distribution of the middle section 140 of the liner 100, e.g. such that the minor axis of the front ring is rotationally aligned with the ribs 146, which may cause the two features to oppose each other's intended effect.

To prevent this issue of possible misalignment, a preferred embodiment of the breast interface 70 may feature a liner 100 whose front section 110 includes an annular groove 126 with (a circumferential shape having) x axes/lines of symmetry, and a liner support frame 200 including an annular front ring 204 with (a circumferential shape having) y axes/lines of symmetry, wherein x<y. In such a preferred embodiment, both the asymmetries related to the wall stiffness distribution and the shape difference between the annular groove 126 and the front ring 204 to promote a controlled bilateral collapse of the liner may be embedded in the liner 100 upon manufacture, which obviates the issue of possible rotational misalignment between the liner 100 and the liner support frame 200 by the user upon assembly. In one preferred embodiment, for example, the liner 100 may have a front section including a non-circular, e.g. elliptical (two lines of symmetry) or oval (one line of symmetry), annular groove 126, and a liner support frame 200 with a circular front ring 204 (infinite lines of symmetry) for insertion therein. Such a liner embodiment 100 is illustrated in FIG. 3. In the rear view of FIG. 3D, the major and minor axes $A_{maj}$, $A_{min}$ of the elliptical annular groove 126 are identified, as well as two opposite ribs 146 extending in the wall parts 142, 144 of the middle section 140. As can be seen, the minor axis $A_{min}$ of the elliptical annular groove 126 is rotationally aligned with the direction in which the ribs 146 are spaced apart, such that insertion of the front ring 204 of the liner support frame 200 in the annular groove 126 of the front section 110 of the liner 100 will cause the liner to be pre-stressed along the minor axis $A_{min}$ to promote collapse of the liner along the major axis $A_{maj}$. In another embodiment, the liner may have a front section including a rectangular, non-square groove (two lines of symmetry), and a liner support frame with a square front ring (four lines of symmetry).

In general, it may be desirable for a user to be able to monitor the breast, and in particular the nipple, during operation. To this end, the liner 100 may be transparent while the liner support frame 200 may include an open frame structure with arms 210a, 210b that define access windows 212 to allow for visual inspection of the interior liner support frame space 202, as is described in more detail below. However, in case the arms 210a, 210b of the liner support frame 200 are accidentally rotationally aligned with the non-collapsing wall part portions of the middle section 140 of the liner 100, the arms 210a, 210b may obstruct a good view of the breast through these non-collapsing wall part portions. To help a user assemble the breast interface 70 in such a manner that the non-collapsing wall portions are visibly positioned in front of the access windows 212, the liner 100, and in particular the front section 110 thereof, may be provided with at least one mark 128 that is to be rotationally aligned with an arm 210a, 210b of the liner support frame 200 during assembly. The mark 128 should, of course, be positioned such that rotational alignment of the mark 128 with an arm 210a, 210b results in the desired visibility of non-collapsing wall part portions through the access windows 212. In one embodiment, the number of marks 128 on the liner 100 may correspond to the number of arms 210a, 210b of the liner support frame 200, such that each mark 128 may be aligned with a respective arm 210a, 210b. A mark 128 may take various forms, such as an arrow head embossed on the outside of the liner 100, or a raised surface portion having a (tangential) width approximately equal to that of the arm 210a, 210b to which it must be aligned.

In principle, the central rearward opening 116b defined by the front wall part 112 may have any suitable circumferential shape. In one embodiment, for instance, the central rearward opening 116b may be circular. A circular central rearward opening, however, has a number of drawbacks. One such drawback is related to the fact that, during operation, the breast pump 1 may apply a vacuum to a woman's breast. This vacuum may cause reddening of the skin of the breast, in particular where it makes contact with the circular circumferential edge 114b of the central rearward opening 116b. The reddish imprint of the circumferential edge 114b on the breast may be mistakenly taken for a sign of a fungal infection, such as ring-worm. Another drawback of a circular central rearward opening is that the undercut, defined by the backflow barrier 120 and the base wall part 122, may be significant. This may hinder both removal of the liner 100 from a mould during manufacture, and proper cleaning of the liner after use.

To overcome or at least mitigate these drawbacks, a preferred embodiment of the liner 100 may include a front wall part 112 defining a central rearward opening 116b having a non-circular shape. The opening 116b may, for instance, have the shape of a flower, e.g. a five petalled flower as is clearly visible in FIG. 3C. Different flower shapes, e.g. flower-shapes with a different number of petals and/or petals shaped different from those shown in FIG. 3C, or altogether different shapes, such as that of a star, may be used as well. Due to the radial variations in the profile of the circumferential edge 114b of the opening 116b, the non-circular openings may generally prevent reddish circular imprints on the breast, and facilitate cleaning of the undercut by making it more accessible. A non-circular shape of the rearward central opening 116b may offer the additional benefits that is has a less mechanical appearance, and that it may look decorative and attractive to a woman using the breast pump 1.

The middle section 140 of the liner 100 may comprise two wall parts: (i) an S-curved connecting wall part 142, and (ii) a rearward tapering, funnel-shaped wall part 144. The S-curved connecting wall part may connect (the rear end of) the base wall part 122 of the front section 110 to the wide front end of the funnel-shaped wall part 144 of the middle section 140.

An interior space 180 bounded by the middle section 140 may define a pressure chamber. During use, the vacuum pump 10 of the breast pump 1 may apply a vacuum to the pressure chamber 180, so as to alternatingly cause the middle section 140 of the liner 100 (i) to collapse onto the nipple of a breast, and (ii) to re-establish, or extend back to, its relaxed shape.

The S-curved connecting wall part 142 may serve to facilitate both the collapse of the middle section 140 when the pressure chamber 180 is subjected to the vacuum, and the re-establishment of the relaxed shape thereof once the vacuum is removed. It derives its name from its longitudinal cross-sectional profile (taken in relaxed condition), which, as is best visible in FIG. 2C, may define an S-curve, i.e. a double bend or double fold. The S-curve may be located immediately adjacent to the (rear end of the) base wall part 122 of the front section 110 of the liner 100, and be rotationally symmetric around the longitudinal axis L of the liner 100. The S-curved connecting wall part 142 may effectively provide for excess wall part material that enables the middle section 140 of the liner 100 to be easily deformed, and thus to collapse inwardly, when the pressure chamber 180 is subjected to a vacuum. In addition, it may be configured such that it will deform back to its relaxed shape once the vacuum in the pressure chamber 180 in cancelled.

The middle section 140 of the liner 100 may preferably be configured to ensure its safe, repeatable, bilateral and peristaltic collapse onto the nipple, occurring from the rear to the front. To help ensure such a collapse, one or both wall parts 142, 144 of the middle section 140 may have a stiffness-distribution with two-fold symmetry around the longitudinal axis L. To this end the wall parts 142, 144 may, for instance, include elongate ribs 146, e.g. relatively stiff wall part portions, that extend in a generally radial/longitudinal direction along or within the respective wall parts 142, 144. In one embodiment, such ribs 146 may be formed by relatively thick wall part portions, which offers the advantage that the liner 100 may be manufactured from a single, homogeneous material, or at least a material having an elastic modulus that is homogeneous throughout the wall parts of the liner 100. In another embodiment, the ribs 146 may be effected through the use of at least two constituent materials having a mutually different modulus of elasticity. In such an embodiment, the ribs 146 may be made of a first constituent material, while the adjacent or surrounding portions of the S-curved and/or funnel-shaped wall parts 142, 144 may be made of a second constituent material having a modulus of elasticity that is smaller than that of the first constituent material.

In the embodiment of the liner 100 depicted in FIG. 3, the middle section 140 of the liner includes two, (tangentially) wide and (longitudinally) elongate ribs 146, defined by relatively thick wall part portions of both the S-curved connecting wall part 142 and the funnel-shaped wall part 144. The ribs 146 are positioned on diametrically opposite sides of the middle section 140. When, during use, a vacuum is applied to the pressure chamber 180, the ribbed portions of the wall parts 142, 144 may offer more resistance to collapse than diametrically opposed unribbed portions thereof, such that a bilateral collapse of unribbed portions towards each other is favored.

The rear section 170 of the liner 100 may include a generally axially extending tubular or pipe-shaped wall part, which may be considered to form an extension of the funnel defined by the funnel-shaped wall part 144 of the middle section 140 of the liner. Accordingly, the rear end of the funnel-shaped wall part 144 of the middle section 140 may be connected to the front end of the tubular wall part of the rear section 170.

The tubular wall part of the rear section 170 of the liner 100 may in principle have any suitable inner and/or outer cross-section. The first exemplary embodiment of the liner 100 shown in FIGS. 2-4, for example, has a rear section 170 with generally circular inner and/or outer cross-sections. Alternatively, the tubular wall part of the rear section 170 may, for instance, have generally tear drop-shaped inner and/or outer cross-sections, such as in the fourth exemplary embodiment shown in FIG. 7. The tear drop-shape—which may be defined by a smooth closed plane curve that has one axis of symmetry and that (unlike an oval) is not exclusively convex where the wide part of the curve merges into the narrower part thereof—may assist the aforementioned bilateral collapse of the liner 100 during operation. In an embodiment of the liner 100 with a tubular rear section 170 that includes a tear drop-shaped inner cross-section, the narrow portion of the tear drop shape may fulfil the function of milk gully that guides milk expressed from the breast towards the milk receptacle 50. In such an embodiment, the length of the narrower part of the tear drop-shaped cross-section (measured along the tear drop's axis of symmetry) may increase in the rearward axial direction of the rear section 170, such that the milk gully defined by the narrower part of the tear drop-shaped cross-section may deepen or slope downwardly in the rearward axial direction.

The rear section 170 may further include one or more external, generally annular flanges, which may be formed integrally with the tubular wall part and extend radially outwardly therefrom. A first flange 172 may be provided at the rear end of the tubular wall part. A second flange 174 may be provided in front of the first flange 172, and be axially spaced apart therefrom, or at least from the rear end of the tubular wall part. Both flanges 172, 174 may have an outer diameter that is greater than an inner diameter of the rear ring 206 of the liner support frame 200 to be discussed below. In embodiments comprising both the first and second flange 172, 174, the axial spacing between them may typically correspond to an axial length of the rear ring 206 of the liner support frame 200. The second flange 174 may typically be somewhat wider (in the axial direction) and/or higher (in the radial direction) than the first flange 172. The function of the first and second flanges 172, 174, which may hereafter be referred to as 'sealing lip' and 'finger grip ring' respectively, will also be clarified below, where assembly of the breast interface 70 is discussed.

The liner 100 may be manufactured in one piece from a flexible, preferably resilient material, such as, for instance, a thermoplastic elastomer, rubber, latex, or liquid silicone rubber (LSR). In one embodiment, the liner 100 may be manufactured through injection moulding, in which process the liner may be set or cured in its relaxed condition. The liner material may be transparent, so as to enable a woman to visually monitor what happens inside the liner 100 during use.

Figure 4A:
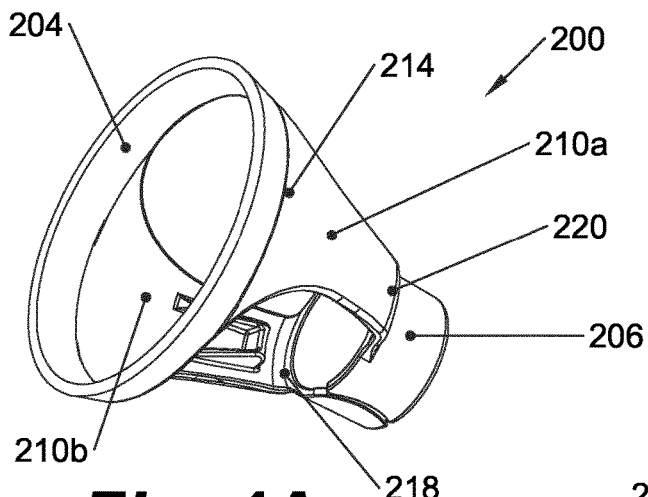
FIGS. 4A-C schematically illustrate the liner support frame of the first exemplary embodiment of the breast interface shown in FIG. 2 in a perspective view (FIG. 4A), a side view (FIG. 4B) and a front view (FIG. 4C), respectively.
Figure 4B:
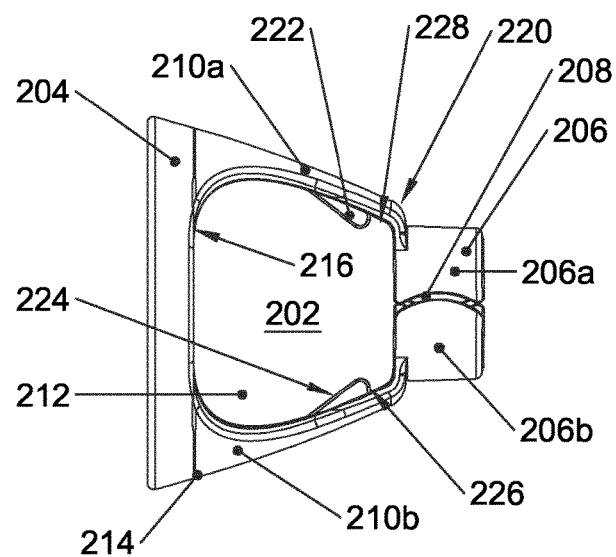
Figure 4C:
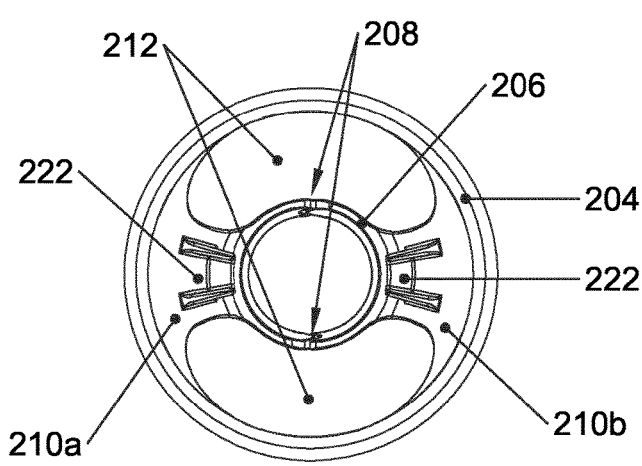

Turning now to a discussion of the construction of the liner support frame 200. FIGS. 4A-C schematically illustrate the liner support frame 200 of the first exemplary embodiment of the breast interface 70 shown in FIGS. 2A-D in a perspective view (FIG. 4A), a side view (FIG. 4B) and a front view (FIG. 4C), respectively.

As its name implies, the liner support frame 200 may serve to provide mechanical support to the liner 100. To this end, it may define an interior liner support frame space 202 in which at least part of the liner 100 is receivable, such that, in an assembled condition of the breast interface 70, the liner 100 is (externally) engaged and framed by the liner support frame 200; see FIGS. 2A-D. In order to fulfil its supportive function, the liner support frame 202 may be made from a relatively stiff material (compared to the liner 100), such that its construction is substantially rigid and capable of withstanding any forces exerted on it by the liner 100 during operation without undergoing substantial deformation. The liner support frame 200 may be manufactured from any suitable material, for example from plastic through injection moulding.

Although the liner support frame 200 may be transparent, and be used in combination with a transparent or non-transparent liner 100, the combination of a transparent liner 100 and an opaque liner support frame 200 may provide for maximum user functionality and an optimal contrast between the two parts, which contrast improves the abilities of the user to assemble the breast interface 70 and to confirm the correctness of an assembly.

The liner support frame 200 may include two axially spaced-apart rings: a front ring 204 and a rear ring 206. For clarity, it is noted that the term 'ring' as used in this text is to be construed broadly; the term is intended to encompass any continuous and discontinuous/split annular element, irrespective of its circumferential shape, which may typically be circular, but may alternatively be non-circular, e.g. polygonal. The two rings 204, 206 may be interconnected by at least one relatively stiff, generally axially extending arm or strut. In the first exemplary embodiment of FIGS. 4A-C, the liner support frame 200 includes two stiff but resilient arms 210a, 210b, which are structionally identical. The front ring 204 may typically have larger inner and outer diameters than the rear ring 206; in embodiments with multiple arms 210a, 210b, the arms 210a, 210b interconnecting the two rings 204, 206 may thus be considered to extend from the front ring 204 to converge in the rearward direction, on the rear ring 206. The inner diameter of the rear ring 206 may be tailored to, i.e. be approximately equal to, the outer diameter of the tubular rear section 170 of the liner 100, which it may be configured to fittingly receive so as to enable a vacuumtight connection to the coupler 30 (see FIGS. 2A-D).

Figure 5A:
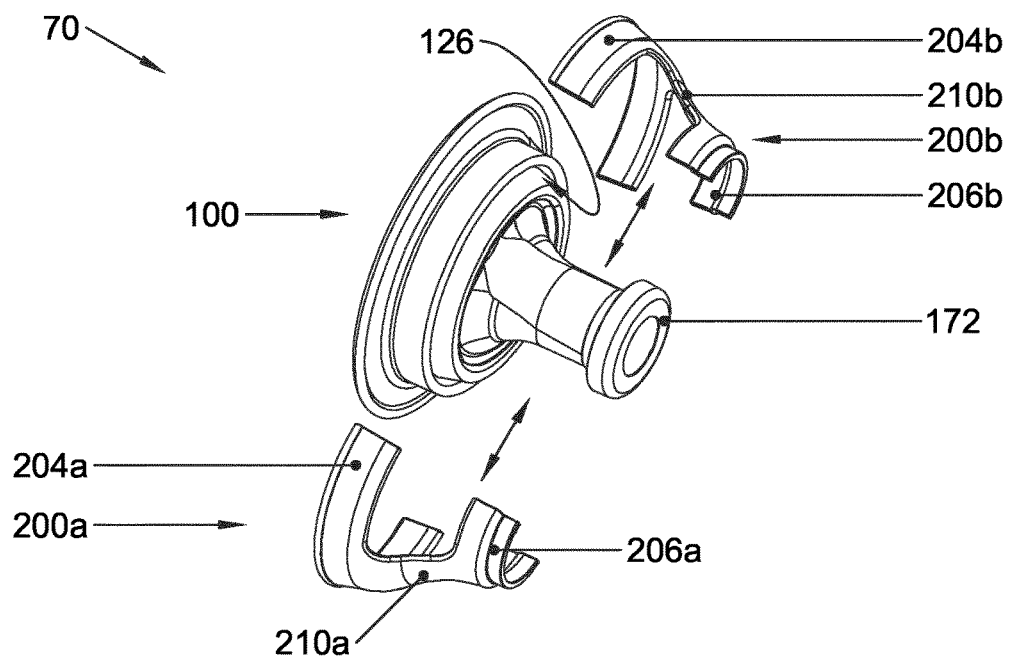
FIGS. 5A-B schematically illustrate in two perspective views a second exemplary embodiment of the breast interface according to the present disclosure, wherein the liner support frame includes two detachable complementary halves.
Figure 5B:
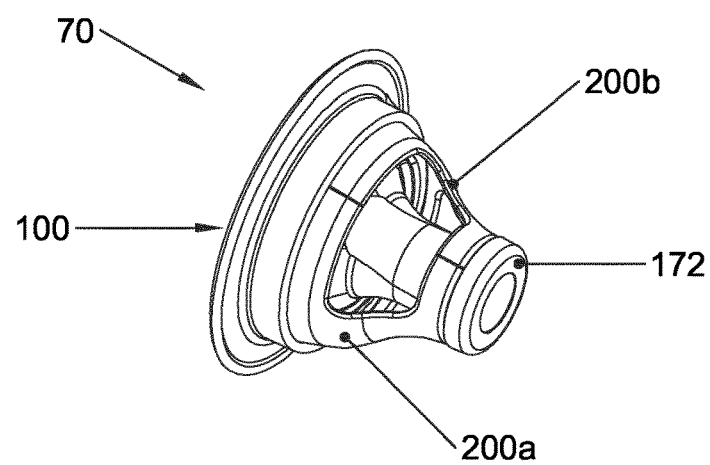
Figure 6A:
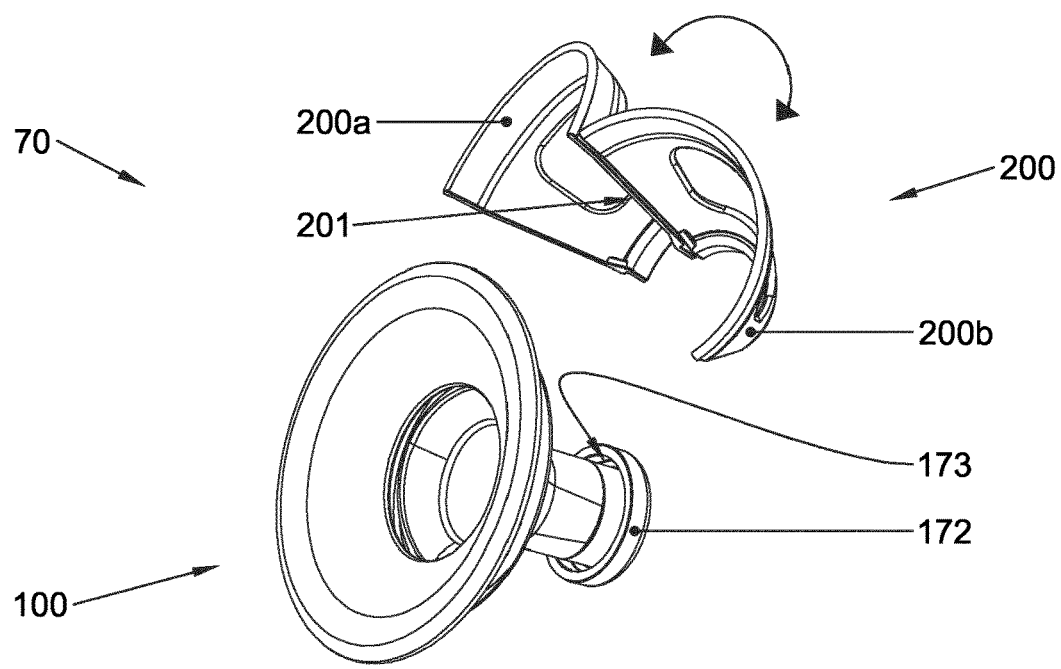
FIGS. 6A-B schematically illustrate in two perspective views a third exemplary embodiment of the breast interface according to the present disclosure, wherein the liner support frame includes two hingeably connected complementary halves.
Figure 6B:
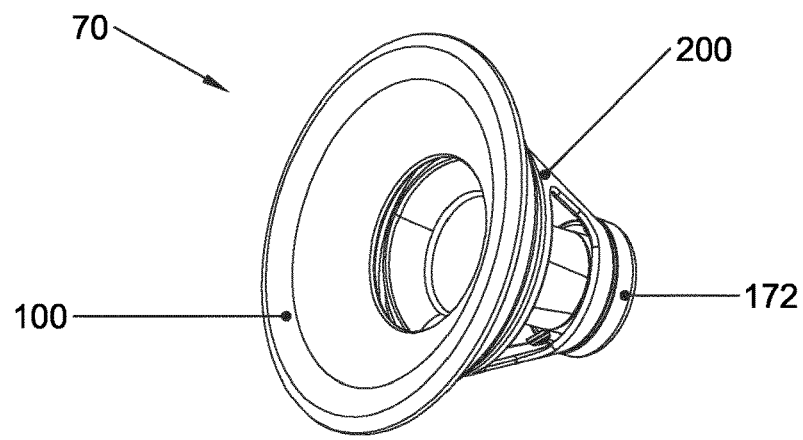

As in the first exemplary embodiment of FIGS. 4A-C, the front ring 204, which may be configured to be received in the annular groove 126 in the front section 110 of the liner 100, may be a single-part, continuous or closed ring (cf. the second and third exemplary embodiments of FIGS. 5 and 6, in which the front ring is split). A generally axial length of the front ring 204 may preferably correspond to a generally axial length of at least one of the walls parts 122, 124 defining the annular groove 126, such that, in an assembled condition of the breast interface 70, the rear end of the front ring 204 (disregarding the joins the with arms 210a, 210b) is substantially flush with at least one of said wall parts, i.e. with at least one of the rear end of the lip wall part 124 and the rear end of the base wall part 122. In the depicted embodiment, the rear end of the front ring 204 sits flush with the rear end of the base wall part 122, as is best seen in the cross-sectional side view of FIG. 2D. During assembly, the flushness of the rear ends provides a cue to the user that insertion of the front ring 204 into the annular groove 126 has been completed.

The rear ring 206, which may be configured to fittingly, and possibly clampingly, engage the tubular rear section 170 of the liner 100, preferably such that it itself is snugly receivable axially in between the two flanges 172, 174 of the rear section (see FIGS. 2A-D), may preferably be a split or double-discontinuous ring. That is, the rear ring 206 may include at least two circumferential discontinuities that split the rear ring into at least two substantially rigid, complementary circumferential portions that are movable and therefore rearrangeable relative to each other, and optionally even detachable from one another, so as to enable a cross-sectional opening/passage area of the ring 206 to be temporarily enlarged. In the first exemplary embodiment of FIGS. 4A-C, for instance, the rear ring 206 has two circumferential discontinuities in the form of actual splits or slits that split the ring into two separate complementary halves 206a, 206b. Leaping ahead with a reference to the second and third exemplary embodiments of FIGS. 5 and 6, it is noted that both these embodiments similarly include a split rear ring 206. Having regard to the embodiment of FIG. 6, it may be noted that hinges that hingeably connect complementary rear ring portions, such as the foil hinge 201 in FIG. 6, may generally be regarded to form a circumferential discontinuity. This is because hinges—even when they do contribute to the definition of the circumferential shape of the rear ring 206—represent a discontinuity in the substantial rigidity of the rear ring along its (inner) circumference; i.e. hinges merely purposefully connect two substantially rigid complementary circumferential rear ring portions to enable their spatial re-arrangement.

As in the first exemplary embodiment of FIGS. 4A-C, the respective complementary rear ring portions 206a, 206b may be connected to the front ring 204 via different arms 210a, 210b. Even though the liner support frame 200 is relatively stiff, this split rear ring construction may facilitate assembly of the breast interface 70 by allowing the complementary circumferential portions of the rear ring 206a, 206b to be radially/tangentially separated (against a modest radially inward spring action exerted by the respective arms 210a, 210b, which are then flexed radially outwards), so as to simplify the task of axially passing the tubular rear section 170 of the liner 100 between them. This is particularly relevant in embodiments including a flange or sealing lip 172 at the rear end of the tubular rear section 170 of the liner 100.

The at least two aforementioned circumferential discontinuities in the split rear ring 206 may be formed by respective splits 208 that separate the it into two complementary portions 206a, 206b. The splits 208 may have identical profiles, as in the depicted embodiment, but this is not necessary. The profile of a split 208 between two complementary circumferential rear ring portions 206a, 206b may in principle have any suitable shape. In one embodiment, a split's profile may be straight or linear. A straight split profile, however, has the disadvantage that it facilitates relative axial movement between the complementary circumferential portions 206a, 206b of the rear ring 206, which may lead to undesirable mechanical stress in the liner support frame 200. Such relatively axial movement may in particular occur upon connection of the breast interface 70 to the breast pump 1, i.e. when the rear end of the breast interface 70 is pressed into the reception passage 42 of the coupler 30. Another drawback of the straight split profile is that it may seem as if the rear ring 206 has been broken accidentally. To overcome these disadvantages, a split's profile may be generally C-shaped, as shown in the depicted embodiment. A smooth C-shaped split profile helps to maintain correct relative axial alignment of the complementary circumferential rear ring portions 206a, 206b, and appears intended such that the rear ring 206 not incorrectly regarded as broken.

A (radially) inner surface of the rear ring 206 may be smooth. A smooth inner surface, however, has been found to promote friction between the rear section 170 of the, for instance silicone, liner 100 and the rear ring 206, which may complicate assembly of the breast interface 70. In order to decrease friction between the rear section 170 of the liner 100 and the inner surface of the rear ring 206, the latter may be provided with a surface texture, e.g. such that is has a matte finish. The surface texture may be a sparked finish.

Together, the arms 210a, 210b of the liner support frame 200 may preferably not fully tangentially or circumferentially enclose the interior liner support frame space 202 of the liner support frame 200. Arms 210a, 210b that together fully enclose the liner support frame space 202 may hinder assembly and disassembly of the breast interface 70, and potentially obstruct a user's view of the liner 100 during use, which view may provide information about, inter alia, the process of liner collapse, and, in embodiments with a transparent liner, nipple placement and milk flow. Accordingly, at least one of the arms 210a, 210b of the liner support frame 200 may preferably define at least one access window 212. More specifically, two tangentially adjacent arms 210a, 210b may together define an access window 212 (tangentially) between them, which access window 212 may allow for manual and visual access to the interior liner support frame space 202. The embodiment of the liner support frame 200 depicted in FIGS. 4A-C has two such access windows on opposite sides of the frame 200. During assembly, one access window 212 may be used for visually monitoring the interior liner support frame space 202, while the other access window 212 may be used for manual access thereto.

To increase the robustness of the liner support frame 200, a join or connection between a respective arm 210a, 210b and the front ring 204 may preferably be (tangentially) wider than a join between the respective arm and the rear ring 206. Accordingly, the (tangential) width of the arm 210a, 210b may taper in the rearward direction. In addition or alternatively, the join at the front ring 204 may preferably define a relatively large radius of curvature 216, e.g. a radius of curvature that is at least half the radius of the front ring 204. Such a large radius may increase the stiffness of the arm 210a, 210b against flexing, and thus make the breast interface 70 feel less floppy during use.

Where an arm 210a, 210b of the liner support frame 200 joins the rear ring 206 thereof, it may preferably define a shoulder 220, which may be characterized by a relatively sharp change in angle. The shoulder 200 may serve as a stop that, during insertion of the rear of the breast interface 70 into the reception passage 42 in the coupler 30 of the breast pump 1, may be forced against the coupler's outer surface. The presence of the shoulder 220 may encourage a user to force the rear of the breast interface into the reception passage 42 present coupler, up until the point where the shoulder 220 abuts the latter, such that a proper vacuum seal is achieved between the breast interface 70 and the coupler 30, and such that the split rear ring 206 of the breast interface 70 is secured in place to provide the liner support frame 70 with part of its rigidity.

Each of the arms 210a, 210b of the liner support frame 200 may be provided with a flange interaction member 222 that is configured for cooperation with the second flange 174 on the rear section 170 of the liner 100. A flange interaction member 222 may protrude inwardly from an inner surface of the arm 210a, 210b on which it is provided. Seen in a longitudinal cross-sectional side view (see FIG. 2C), the flange interaction member 222 may be generally sawtooth-shaped, and include a sloping side 224 that, seen in the rearward direction, ramps radially inwardly, and a rear stop side 226 that extends substantially radially. The stop side 226 may be disposed adjacent to, but axially spaced apart from, the front end of the rear ring 206, such that an axial gap 228 exists between the stop side 226 and the front end of the rear ring 206. In embodiments where the join between an arm 210a, 210b and the rear ring 206 of the liner support frame defines a shoulder 220, the stop side 226 of the flange interaction member 222 may face the inner side of the shoulder 220.

The flange interaction member(s) 222 may serve multiple purposes, as will become clear from a description of the process of assembly of the first exemplary embodiment the breast interface 70.

In case the breast interface 70 comprises the liner 100 and the liner support frame 200 as separate structural components, the breast interface of FIGS. 2-4 may be assembled as follows. A user may axially insert the tubular rear section 170 of the liner through the front ring 204 of the liner support frame 200, such that any marks 128 provided on the liner 100 are in rotational alignment with the arms 210a, 210b thereof. The user may then reach through one or more of the access windows 212 provided in the liner support frame 200, and grip the second flange or finger grip ring 174 provided on the rear section 170 of the liner 100. Holding the second flange 174, the user may push or pull the liner 100 rearward. In doing so, the second flange 174 may come into contact with the flange interaction members 222 provided on the inner surfaces of the arms 210a, 210b, as a result of which the arms 210a, 210b of the liner support frame 200 may be forced to progressively spread radially apart as the liner 100 is moved further rearward. The spreading of the arms 210a, 210b entails the spreading of the complementary circumferential portions 206a, 206b of the split rear ring 206 of the liner support frame 200, which facilitates passing of the first flange 172 between them. Once the second flange 174 reaches the axial position of the stop sides 226 of the flange interaction members 222, the second flange may snap into the axial gap 228 between the stop side 226 and the front end of the rear ring 206; at the same moment, the two arms 210a, 210b may relax again and move towards each other, such that the complementary circumferential rear ring portions 206a, 206b fittingly engage the portion of the tubular rear section 170 of the liner 100 extending between the first and second flanges 172, 174. Not only does this provide visual confirmation to the user that insertion of the liner 100 into the liner support frame 200 is complete, at least at the rear end, it also locks the sealing lip 172 and the finger grip ring 174, and hence the liner 100, against further axial displacement. To complete the assembly, the user may verify that the front ring 204 of the liner support frame 200 has been properly received in the annular groove 126 in the front section 100 of the liner 100, and, where necessary, still ensure proper seating of the front ring 204 therein, preferably such that the front ring 204 is flush with a rear end of at least one of the wall parts 122, 124 that define the groove 126.

Once the breast interface 70 itself has been assembled, its rear portion, in particular the tubular rear section 170 of the liner 100 and the rear ring 206 of the liner support frame 200, may be inserted into the reception passage 42 provided by the coupler 30 of the breast pump 1. The reception passage 42 may preferably be dimensioned to press-fittingly receive the rear portion of the breast interface 70, such that proper vacuum sealing is accomplished.

A primary vacuum seal between the breast interface 70 and the coupler 30 may be formed between the sealing lip 172 and an inner surface of the reception passage 42. To this end, an outer diameter of the sealing lip 172 may preferably be slightly larger than an inner diameter of the reception passage 42. Due to the flexible nature of the liner material, the sealing lip 172 may then deform upon insertion of the rear portion of the breast interface 70 into the reception passage 42, thereby accommodating any differences in shape between the outer circumference of the sealing lip 172 and the inner circumference of the reception passage 42, and thus creating an effective vacuum seal. A secondary vacuum seal may be formed between an outer surface of the split rear ring 206 and the inner surface of the reception passage 42. In order to achieve this secondary vacuum seal, the surfaces of the two typically rigid components 42, 206 must be substantially identical in shape, e.g. have a same diameter, taper, etc. A tertiary vacuum seal may be formed by the sealing lip 172 in cooperation with the finger grip ring 174, as the two engage the rear ring 206 axially in between them.

Now that a first exemplary embodiment of the breast interface 70 has been described above with reference to FIGS. 1-4, attention is invited to a number of further exemplary embodiments that illustrate some particular and advantageous variations.

Although the liner support frame 200 of the first exemplary embodiment of FIGS. 1-4 is a single part-component, it is understood that the liner support frame 200 of alternative embodiments may include multiple, detachably connectable parts.

In one embodiment (not shown), for instance, the at least one arm interconnecting the front ring and the rear ring may subtend an angle in the range of 120°-180° with respect to a longitudinal axis of the liner support frame over substantially the arm's entire axial length. Such a wide, 'half-pipe' arm may provide for a cradle-like liner receptacle with sufficient rigidity to render additional arms superfluous. In such an embodiment, the front ring 204 and/or the rear ring 206 may comprise two detachably connectable complementary circumferential portions. For each ring, one of the complementary circumferential portions may be integrated with the half-pipe arm, while the other may be detachably connectable thereto, e.g. in the form of a clip. In a disconnected condition of the latter ring portion, insertion of the liner 100 in the former arm-attached portion is facilitated, while in a closed condition of both portions, the liner may be firmly held in place between them.

In an elaboration of this latter embodiment, such as the second exemplary embodiment of FIG. 5, the entire liner support frame 200 may be split into two detachably connectable portions or halves 200a, 200b. As depicted, in this embodiment both the front ring 204 and the rear ring 206 may be split, and each ring 204, 206 may have one portion 204a, 206a that is fixedly connected to a first arm 210a, and another complementary portion 204b, 206b that is fixedly connected to a second arm 210b. During assembly of the breast interface 70, the two frame portions or halves 200a, 200b may be brought into engagement with the liner 100 in turn, in particular by (i) positioning their front ring portions 204a, 204b in the annular groove 126 of the liner 100 and (ii) positioning the rear edges of their rear ring portions 206a, 206b against the sealing lip 172, possibly in an annular groove 173 defined thereby (see FIG. 6A). Subsequently, the breast interface 70 may be push-fitted into the reception passage 42 provided by the coupler 30 of the breast pump 1.

Although the two-part liner support frame 200 of FIG. 5 overcomes the need for a user to exert substantial force to insert the sealing lip 172 through the rear ring 206 during assembly of the breast interface 70, the multi-part design of the liner support frame 200 entails the drawback that different parts of the frame may not be kept together and may inadvertently be lost. To avoid this problem, the two complementary halves 200a, 200b of the liner support frame may not be made detachably connectable, but instead be hingeably connected, for instance by means of a foil hinge 201, as in the third exemplary embodiment of FIG. 6.

Figure 7A:
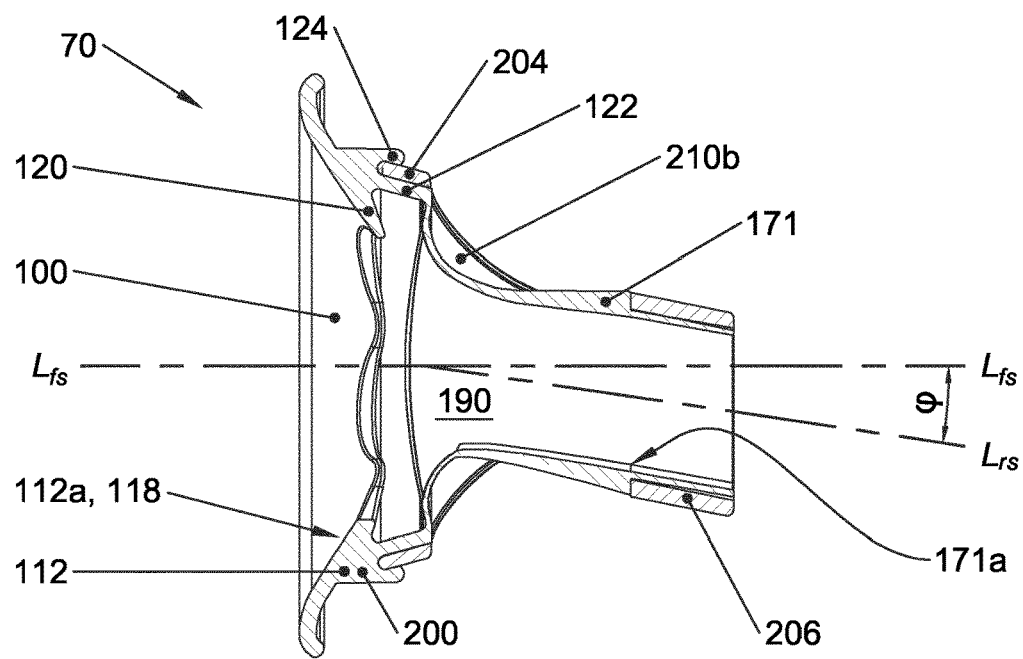
FIGS. 7A-B schematically illustrate in a cross-sectional side view (FIG. 7A) and a rear view (FIG. 7A) a fourth exemplary embodiment of the breast interface according to the present disclosure, wherein the liner includes a tubular rear section having a tear drop-shaped inner cross-sectional profile.
Figure 7B:
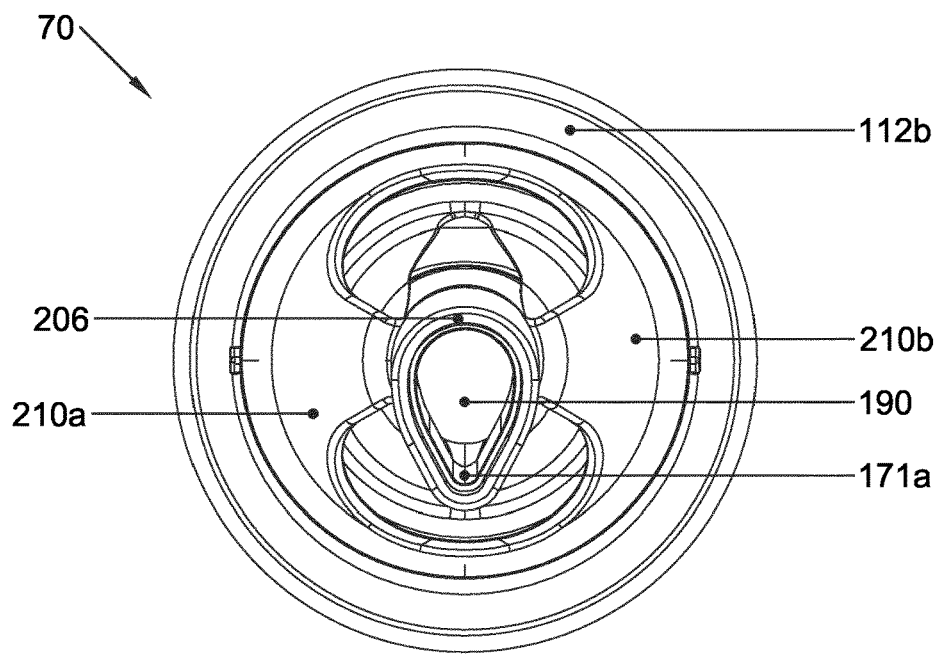

FIGS. 7A-B schematically illustrate a fourth exemplary embodiment of the breast interface 70 according to the present disclosure in a cross-sectional side view (FIG. 7A) and a rear perspective view (FIG. 7B).

A problem associated with the first exemplary embodiment of the breast interface 70 of FIGS. 1-4 is that it may require a woman using it to lean forward, so as to ensure that milk expressed from her breast flows towards and into the milk receptacle 50. The forward leaning posture may become uncomfortable as a single milk-expressing session may last a while, sometimes in excess of half an hour.

To overcome the problem of discomfort, the breast interface 70, and in particular the liner 100 thereof, may be associated with a use orientation in which it has an upper or top side and a lower or bottom side. In addition, the front section 110 of the liner 100 may be associated with a longitudinal axis $L_{fs}$, which may extend substantially perpendicular to a plane of the opening 116b in the breast contact surface 118 (see also FIG. 2C), and—in said use orientation—substantially horizontally. I.e., during use, when the breast contact surface 118 of the front section 110 is in contact with a woman's breast, the longitudinal axis $L_{fs}$ of the front section 110 may extend substantially horizontally. The construction of the liner 100 may further be adapted such that the rearward tapering, funnel shaped wall part 144 of the middle section 140 and/or the tubular wall part 171 of the rear section 170 of the liner 100 define a milk conduit 190 that extends from the (nipple receiving) opening 116b in the breast contact surface 118 to a rear end (milk discharge) opening of the tubular wall part 171, and that is at least partially bounded by an elongate inner lower/bottom surface portion 171a that—in the aforementioned use orientation—slopes downwardly relative a longitudinal axis $L_{fs}$ of the front section 110. Due to the downward slope of the (bottom surface portion 171a) of the rear section 110, milk expressed from the breast will naturally flow through tubular wall part 171 of the rear section 170 under the action of gravity, towards the rear end opening thereof, thus obviating the need for woman to lean forward during use.

In accordance with this solution, a longitudinal axis L of the breast interface 70 may include a (downward) kink or bend, preferably such that the longitudinal axis L of the breast interface 70 includes two straight, non-aligned sections; see FIG. 7A. A first section $L_{fs}$ of the longitudinal axis may be associated with the front section 110 of the liner 100 and the front ring 204 of the liner support frame 200, while a second section L of the longitudinal axis may be associated with the rear section 170 of the liner 100, and with the at least one arm 210a, 210b and rear ring 206 of the liner support frame 200. The two sections $L_{fs}$, $L_{rs}$ of the longitudinal axis L of the breast interface 70 may preferably include an angle in the range of about 10-45 degrees. The cross-sectional shape of at least the tubular wall part 171 of the rear section 170 may be circular, but need not be. In the depicted embodiment, for instance, the tubular wall part 171 of the rear section 170 has an (inverted) tear drop-shaped inner cross-sectional profile, as discussed above and shown in FIG. 7B. The tubular wall part 171 thus defines a longitudinal portion of the milk conduit 190 with a 'downwardly sloping gully', the bottom of which is formed by the elongate bottom surface portion 171a.

Although illustrative embodiments of the presently disclosed breast interface have been described above, in part with reference to the accompanying drawings, it is to be understood that the disclosure is not limited to these embodiments. Variations to the disclosed embodiments can be understood and effected by those skilled in the art in practicing the breast interface, from a study of the drawings, the disclosure, and the appended claims. Reference throughout this specification to "one embodiment", "an embodiment" and the like means that a particular feature, structure or characteristic described in connection with the embodiment may be included in at least one embodiment of the breast interface. Thus, the appearances of the phrases "in one embodiment" or "in an embodiment" in various places throughout this specification are not necessarily all referring to the same embodiment. Furthermore, it is noted that particular features, structures, or characteristics of one or more embodiments may be combined in any suitable manner to form new, not explicitly described embodiments. Likewise, particular features, structures, or characteristics of one or more embodiments may be removed from explicitly described embodiments in order to form new, not explicitly described embodiments. For example, the feature of the 'downward sloping rear section' of the liner described above with reference to the fourth exemplary embodiment of FIG. 7 may be included in any of the other embodiments described, so as to form new embodiments; similarly, it is contemplated that features described above with reference to other embodiments may be included in the fourth embodiment to form new not explicitly described embodiments.

LIST OF ELEMENTS 1 breast pump
10 vacuum pump
30 coupler
32 first tubular segment
34 first channel
36 second tubular segment
38 second channel
40 threaded socket at lower end of first tubular segment
42 reception passage for receiving rear end of breast interface
50 milk receptacle
70 breast interface
100 liner
110 front section
112 conical front wall part
112a,b front side (a) and rear side (b) of front wall part
114a,b radially outer (a) and radially inner (b) circumferential edge
116a,b forward opening (a) and rearward opening (b)
118 breast contact surface
120 backflow barrier
122 base wall part
124 lip wall part 126 annular groove between base wall part and lip wall part
128 rotational alignment mark
140 middle section
142 S-curved connecting wall part
144 rearward tapering, funnel-shaped wall part
146 longitudinal rib
170 rear section
171 tubular wall part
171a lower inner surface portion
172 first flange/sealing lip
173 annular groove defined by forward bent first flange
174 second flange/finger grip ring
180 interior pressure chamber
190 milk passage
200 liner support frame
200a,b first (a) and second (b) complementary portion of liner support frame
201 (foil) hinge
202 interior liner support frame space
204 front ring
204a,b first (a) and second (b) complementary front ring portions
206 split rear ring
206a,b first (a) and second (b) complementary rear ring portions
208 split between ring halves
210a,b first (a) and second (b) arm
212 access window between first and second arms
214 join between arm and front ring
216 large radius at join between arm and front ring
218 join between arm and rear ring
220 shoulder
222 flange interaction member
224 sloping side
226 stop side
228 axial gap between stop side and front end of rear ring
$A_{maj}$ major axis of elliptical annular groove
$A_{min}$ minor axis of elliptical annular groove
L longitudinal axis of breast interface
$L_{fs}$ longitudinal axis of front section of liner/front ring of frame
$L_{rs}$ longitudinal axis of rear section of liner/arms and rear ring of frame
R radial direction
φ angle included by longitudinal axis sections $L_{fs}$, $L_{rs}$

The invention claimed is:

1. A liner for use in a breast interface, said liner including:
a front section including a front wall part defining a breast contact surface and an opening provided in said breast contact surface, said breast contact surface being configured to be placed about a woman's breast during use, while a nipple of the woman's breast protrudes at least partially through said opening;
a rear section including a tubular wall part having a rear end opening; and
a middle section, interposed between the front section and the rear section, configured to collapse bilaterally onto the nipple during operation, wherein the middle section couples to a rear end of the front section and is further configured for being (i) one of stretched or widened along a first radial direction and (ii) one of compressed or narrowed along a second radial direction substantially perpendicular to the first radial direction, to ensure that the middle section collapses bilaterally onto the nipple during operation,
wherein the front section, the middle section and the rear section together at least partly define a milk passage that extends from the opening in the breast contact surface of the front section to the rear end opening of the tubular wall part of the rear section, and
wherein the liner is associated with a use orientation in which a longitudinal axis of the front section extends substantially horizontally, while the tubular wall part of the rear section comprises (i) a lower inner surface portion that partially bounds the milk passage, and (ii) a longitudinal axis of the tubular wall part of the rear section that in said use orientation, seen in a rearward direction slopes downwardly relative to the longitudinal axis of the front section that extends substantially horizontally, wherein the tubular wall part of the rear section further comprises a tear drop-shaped cross-section having one axis of symmetry and a narrower part that defines a gully, wherein the narrower part of the tear drop-shaped cross-section that defines the gully assists the middle section collapse bilaterally onto the nipple during operation, and whose bottom is defined by the lower inner surface portion of the tubular wall part of the rear section, further wherein a length of the narrower part of the tear drop-shaped cross-section, measured along the one axis of symmetry and relative to the longitudinal axis of the front section that extends substantially horizontally, increases in the rearward direction, such that the gully deepens in the rearward direction.

2. The liner according to claim 1, wherein the longitudinal axis of the front section extends substantially perpendicular to a plane of the opening in the breast contact surface.

3. The liner according to claim 1, wherein the lower inner surface portion extends over substantially an entire length of the tubular wall part of the rear section.

4. The liner according to claim 1, where the lower inner surface portion slopes downwardly relative to the longitudinal axis of the front section at a substantially constant slope angle.

5. The liner according to claim 1, wherein—in said use orientation—the lower inner surface portion has an average downward slope angle in the range of 10-45 degrees relative to the longitudinal axis of the front section.

6. The liner according to claim 1, wherein the front section of the liner includes an annular base wall part that connects to a rear side of the front wall part, at a radial position in between those of forward and rearward circumferential edges thereof, and extends from the rear side of the front wall part in a rearward direction, wherein the front wall part extends radially inwardly beyond the annular base wall part, so as to form an annular backflow barrier.

7. The liner according to claim 1, wherein the middle section, interposed between the front section and the rear section, connects the rear section to the front section, the middle section further including a rearward tapering, funnel shaped wall part.

8. The liner according to claim 1, wherein the middle section further comprises (a)(i) an S-curved connecting wall part and (a)(ii) a funnel-shaped wall part, wherein the S-curved connecting wall part is located immediately adjacent a base wall part of the front section and connects the base wall part of the front section to a wide front end of the funnel-shaped wall part, wherein an opposite end of the funnel-shaped wall part is narrower than the wide front end, and wherein the S-curved connecting wall part facilitates both (b)(i) a collapse of the middle section from a relaxed shape in response to an application of vacuum internal to the middle section and (b)(ii) re-establishment of the relaxed shape upon removal of the vacuum internal to the middle section.

9. The liner according to claim 8, further wherein the middle section is configured to ensure repeatable, bilateral and peristaltic collapse onto the nipple, occurring from a rear to a front of the nipple.

10. The liner according to claim 8, wherein one or both of the S-curved connecting wall part and the funnel-shaped wall part further comprise a stiffness-distribution with two-fold symmetry around the longitudinal axis of the front section, the stiffness-distribution being provided via one or more ribs that comprise elongate wall part portions, extending in a radial or longitudinal direction along or within a respective one or both S-curved connecting wall part and funnel-shaped wall part.

11. The liner according to claim 10, wherein the one or more ribs comprise ribs positioned on diametrically opposite sides of the middle section, further wherein the ribs provide more resistance to collapse than diametrically opposed unribbed portions of the middle section, such that a bilateral collapse of unribbed portions of the middle section towards each other is favored.

12. The liner according to claim 8, wherein the narrower part of the tear drop-shaped cross-section of the rear section contributes to a bilateral collapse of the middle section during operation.

13. A breast interface for a breast pump, including:
a liner support frame defining an interior liner support frame space configured to receive at least part of the liner according to claim 1, said liner support frame including:
a front ring;
a rear ring; and
at least one arm interconnecting the front ring and the rear ring such that the front ring is axially spaced apart from the rear ring;
wherein the front section of the liner is configured to engage the front ring of the liner support frame, while the tubular wall part of the rear section of the liner is configured to be fittingly received by the rear ring of the liner support frame.

14. The breast interface according to claim 13, wherein a rear end of the tubular wall part of the rear section of the liner is provided with a first annular flange that has an outer diameter that is greater than an inner diameter of the rear ring of the liner support frame, and that, in an assembled condition of the breast interface, the first annular flange abuts an end of the rear ring, and
wherein the rear ring is a split rear ring including at least two complementary circumferential rear ring portions that are rearrangeable relative to each other to facilitate passage of a flanged rear end of the liner.

15. The breast interface according to claim 13, wherein the at least one arm comprises two tangentially adjacent and axially extending resilient arms that together define an access window tangentially between the two tangentially adjacent and axially extending resilient arms, wherein the access window enables a manual and a visual access to the interior liner support frame space.

16. The breast interface according to claim 15, wherein the liner further comprises a transparent liner and the liner support frame further comprises one of a transparent and an opaque liner support frame.

17. The breast interface according to claim 15, wherein the two tangentially adjacent and axially extending resilient arms define two access windows, and wherein non-collapsing wall portions of the middle section of the liner are visibly positioned in front of a respective access window.

18. The breast interface according to claim 17, wherein the front section of the liner further comprises at least one mark that is to be rotationally aligned with a corresponding one of the at least one arm of the liner support frame for use during assembly to assist in a positioning of the non-collapsing wall portions of the middle section of the liner in front of the respective access window.

19. The breast interface according to claim 13, wherein the rear section of the liner comprises a finger grip ring flange, and wherein each of the at least one arm further comprises a flange interaction member configured to cooperate with the finger grip ring flange, the flange interaction member including (i) a sloping side protruding radially inwardly from an inner surface of each of a respective at least one arm and (ii) a rear stop side extending radially inwardly, wherein the rear stop side is disposed adjacent to, but axially spaced apart from, a front end of the rear ring, wherein an axial gap between the rear stop side and the front end of the rear ring is configured to removeably receive the finger grip ring flange in response to inserting the liner within the liner support frame.

20. A breast pump including a breast interface according to claim 13.

* * * * *